US010072294B2

(12) United States Patent
Yen et al.

(10) Patent No.: US 10,072,294 B2
(45) Date of Patent: Sep. 11, 2018

(54) ULTRA-HIGH SENSITIVE MONITORING OF EARLY TRANSPLANTATION FAILURE

(75) Inventors: Yun Yen, Arcadia, CA (US); Qiang Liu, Upland, CA (US); Fouad Kandeel, Duarte, CA (US); Kevin Ferreri, Duarte, CA (US); Steve S. Sommer, Duarte, CA (US); Rasha Shehatta, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 670 days.

(21) Appl. No.: 14/000,485

(22) PCT Filed: Feb. 16, 2012

(86) PCT No.: PCT/US2012/025393
§ 371 (c)(1),
(2), (4) Date: Nov. 25, 2014

(87) PCT Pub. No.: WO2012/115851
PCT Pub. Date: Aug. 30, 2012

(65) Prior Publication Data
US 2015/0126373 A1  May 7, 2015

Related U.S. Application Data

(60) Provisional application No. 61/445,287, filed on Feb. 22, 2011.

(51) Int. Cl.
*C07H 21/04* (2006.01)
*C12Q 1/68* (2018.01)
*C12Q 1/6883* (2018.01)

(52) U.S. Cl.
CPC ..... *C12Q 1/6883* (2013.01); *C12Q 2600/156* (2013.01); *G01N 2510/00* (2013.01)

(58) Field of Classification Search
None
See application file for complete search history.

(56) References Cited

U.S. PATENT DOCUMENTS 8,703,652 B2 * 4/2014 Quake ............... C12Q 1/6837
435/6.11
2006/0292599 A1  12/2006 Ritz et al.
2010/0129871 A1  5/2010 Liu et al.

FOREIGN PATENT DOCUMENTS

EP       1 325 963    *  9/2003  ............... C12Q 1/68

OTHER PUBLICATIONS

Fredriksson et al. (Leukemia, vol. 18, pp. 255-266, 2004).*
Liu et al. (BioTechniques, vol. 36, No. 1, pp. 156-166, 2004).*
Gineikiene et al. (J. of Mol. Diagnostics, vol. 11, No. 1, pp. 66-74, Jan. 2009).*
Shi et al. (Human Mutation, vol. 28, No. 2, pp. 131-136, 2007).*
Milbury et al. (Clinical Chemistry, vol. 55, No. 4, pp. 632-640, 2009).*
Yoon et al. (PLoS, vol. 5, No. 7, e1000558, pp. 1-9, Jul. 2009) (Year: 2009).*
Qin et al. (PLoS Biology, vol. 5, No. 9, pp. e224, Sep. 2007) (Year: 2007).*
Tan et al. (Clinical Chemistry, vol. 52, No. 12, pp. 2250-2257, 2006) (Year: 2006).*
PCT International Search Report, PCT/US12/25393, dated May 25, 2012, International Filing Date: Feb. 16, 2012, Priority Date: Feb. 22, 2011, Applicant: City of Hope, 3 pages.

* cited by examiner

*Primary Examiner* — Jeanine Anne Goldberg
(74) *Attorney, Agent, or Firm* — Rothwell, Figg, Ernst & Manbeck, P.C.

(57) ABSTRACT

The present invention provides a method for detecting transplantation failure of a transplanted organ or cells which comprises detecting a donor-positive but recipient-negative DNA marker in the recipient's plasma using pyrophosphorolysis activated polymerization. Because of the high sensitivity, specificity and selectivity of pyrophosphorolysis activated polymerization, transplantation failure can be detected at early stages and treatment can be initiate earlier.

15 Claims, 9 Drawing Sheets

Specification includes a Sequence Listing.

STEP 1. SCREENING A DONOR-SPECIFIC POLYMORPHISM

DONOR DNA  RECIPIENT DNA

STEP 2. TRACKING THE MARKER IN RECIPIENT BLOOD

A. MISMATCHED GENOMIC DNA

B. NO DNA TEMPLATE

SEQUENCE LISTING

<160> NUMBER OF SEQ ID NOS: 55

<210> SEQ ID NO 1
<211> LENGTH: 52
<212> TYPE: DNA
<213> ORGANISM: Homo sapiens

<400> SEQUENCE: 1
acacagtgcc cttcttgcaa gtactasgac actccaatcc catttctacc tc    52

<210> SEQ ID NO 2
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyC

<400> SEQUENCE: 2
ggcacacagt gcccttcttg caagtactan    30

<210> SEQ ID NO 3
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyG

<400> SEQUENCE: 3
ccctgaggta gaaatgggat tggagtgtcn    30

<210> SEQ ID NO 4
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyG

<400> SEQUENCE: 4
ggcacacagt gcccttcttg caagtactan    30

<210> SEQ ID NO 5
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyC

<400> SEQUENCE: 5
ccctgaggta gaaatgggat tggagtgtcn    30

<210> SEQ ID NO 6
<211> LENGTH: 52
<212> TYPE: DNA
<213> ORGANISM: Homo sapiens

<400> SEQUENCE: 6
cactggacct tacagttctc actgccsttg gactccagtc cagctttggg gc    52

<210> SEQ ID NO 7
<211> LENGTH: 30
<212> TYPE: DNA
<213> ORGANISM: Homo sapiens
<220> FEATURE:
<221> NAME/KEY: misc_feature
<222> LOCATION: (30)..(30)

<223> OTHER INFORMATION: n is dideoxyC

<400> SEQUENCE: 7
cttcactgga ccttacagtt ctcactgccn                                    30

<210> SEQ ID NO 8
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyG

<400> SEQUENCE: 8
cccagcccca aagctggact ggagtccaan                                    30

<210> SEQ ID NO 9
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyG

<400> SEQUENCE: 9
cttcactgga ccttacagtt ctcactgccn                                    30

<210> SEQ ID NO 10
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyC

<400> SEQUENCE: 10
cccagcccca aagctggact ggagtccaan                                    30

<210> SEQ ID NO 11
<211> LENGTH: 52
<212> TYPE: DNA
<213> ORGANISM: Homo sapiens

<400> SEQUENCE: 11
tgacaccaga ggggcttagg cttcttsatc cacagcagag ttttctggga tt           52

<210> SEQ ID NO 12
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyC

<400> SEQUENCE: 12
ttctgacacc agaggggctt aggcttcttn                                    30

<210> SEQ ID NO 13
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyG

<400> SEQUENCE: 13
aagaaatccc agaaaactct gctgtggatn                                30

<210> SEQ ID NO 14
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxy G

<400> SEQUENCE: 14
ttctgacacc agagggctt aggcttcttn                                 30

<210> SEQ ID NO 15
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyC

<400> SEQUENCE: 15
aagaaatccc agaaaactct gctgtggatn                                30

<210> SEQ ID NO 16
<211> LENGTH: 52
<212> TYPE: DNA
<213> ORGANISM: Homo sapiens

<400> SEQUENCE: 16
tcccaagaac acctactaat tcctctscac tccttcatgg ctgggacagt ta       52

<210> SEQ ID NO 17
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyC

<400> SEQUENCE: 17
cggtcccaag aacacctact aattcctctn                                30

<210> SEQ ID NO 18
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyG

<400> SEQUENCE: 18
ccagtaactg tcccagccat gaaggagtgn                                30

<210> SEQ ID NO 19
<211> LENGTH: 30
<212> TYPE: DNA
<213> ORGANISM: Homo sapiens
<220> FEATURE:

```
<221> NAME/KEY: misc_feature
<222> LOCATION: (30)..(30)
<223> OTHER INFORMATION: n is dideoxyG

<400> SEQUENCE: 19
cggtcccaag aacacctact aattcctctn                                              30

<210> SEQ ID NO 20
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyC

<400> SEQUENCE: 20
ccagtaactg tcccagccat gaaggagtgn                                              30

<210> SEQ ID NO 21
<211> LENGTH: 52
<212> TYPE: DNA
<213> ORGANISM: Homo sapiens

<400> SEQUENCE: 21
gccctccttt cccagtccaa ggttgasagg gtcctgtcat ttcctgtccc aa                     52

<210> SEQ ID NO 22
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyC

<400> SEQUENCE: 22
gaagccctcc tttcccagtc caaggttgan                                              30

<210> SEQ ID NO 23
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyG

<400> SEQUENCE: 23
ctacttggga caggaaatga caggaccctn                                              30

<210> SEQ ID NO 24
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyG

<400> SEQUENCE: 24
gaagccctcc tttcccagtc caaggttgan                                              30

<210> SEQ ID NO 25
<211> LENGTH: 30
<212> TYPE: DNA
<213> ORGANISM: Homo sapiens
```

```
<220> FEATURE:
<221> NAME/KEY: misc_feature
<222> LOCATION: (30)..(30)
<223> OTHER INFORMATION: n is dideoxyC

<400> SEQUENCE: 25
ctacttggga caggaaatga caggaccctn                                          30

<210> SEQ ID NO 26
<211> LENGTH: 52
<212> TYPE: DNA
<213> ORGANISM: Homo sapiens

<400> SEQUENCE: 26
gtactttttg gcatgtactc tccacgscat aatttgtaaa tgccctggtc tt                 52

<210> SEQ ID NO 27
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyC

<400> SEQUENCE: 27
tatgtacttt ttggcatgta ctctccacgn                                          30

<210> SEQ ID NO 28
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyG

<400> SEQUENCE: 28
ccgcaagacc agggcattta caaattatgn                                          30

<210> SEQ ID NO 29
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyG

<400> SEQUENCE: 29
tatgtacttt ttggcatgta ctctccacgn                                          30

<210> SEQ ID NO 30
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyC

<400> SEQUENCE: 30
ccgcaagacc agggcattta caaattatgn                                          30

<210> SEQ ID NO 31
<211> LENGTH: 52
<212> TYPE: DNA
```

<213> ORGANISM: Homo sapiens

<400> SEQUENCE: 31
ccaaggggaa tttcagtgca ggatgtsttg tgatgggagt agtgagttag ca    52

<210> SEQ ID NO 32
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyC

<400> SEQUENCE: 32
ataccaaggg gaatttcagt gcaggatgtn    30

<210> SEQ ID NO 33
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyG

<400> SEQUENCE: 33
caaatgctaa ctcactactc ccatcacaan    30

<210> SEQ ID NO 34
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyG

<400> SEQUENCE: 34
ataccaaggg gaatttcagt gcaggatgtn    30

<210> SEQ ID NO 35
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyC

<400> SEQUENCE: 35
caaatgctaa ctcactactc ccatcacaan    30

<210> SEQ ID NO 36
<211> LENGTH: 52
<212> TYPE: DNA
<213> ORGANISM: Homo sapiens

<400> SEQUENCE: 36
taaaattatc cctgggctct cagtaawgcc aattgatgtc atcacttgga ca    52

<210> SEQ ID NO 37
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyA

<400> SEQUENCE: 37
ggctaaaatt atccctgggc tctcagtaan                                    30

<210> SEQ ID NO 38
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyT

<400> SEQUENCE: 38
acactgtcca agtgatgaca tcaattggcn                                    30

<210> SEQ ID NO 39
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyT

<400> SEQUENCE: 39
ggctaaaatt atccctgggc tctcagtaan                                    30

<210> SEQ ID NO 40
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyA

<400> SEQUENCE: 40
acactgtcca agtgatgaca tcaattggcn                                    30

<210> SEQ ID NO 41
<211> LENGTH: 52
<212> TYPE: DNA
<213> ORGANISM: Homo sapiens

<400> SEQUENCE: 41
taccggcaaa gagggaacca gtgagawatc ttgtctcaaa ctctggggct ga            52

<210> SEQ ID NO 42
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyA

<400> SEQUENCE: 42
aattaccggc aaagagggaa ccagtgagan                                    30

<210> SEQ ID NO 43
<211> LENGTH: 30
<212> TYPE: DNA
<213> ORGANISM: Homo sapiens
<220> FEATURE:

```
<221> NAME/KEY: misc_feature
<222> LOCATION: (30)..(30)
<223> OTHER INFORMATION: n id dideoxyT

<400> SEQUENCE: 43
aacatcagcc ccagagtttg agacaagatn                              30

<210> SEQ ID NO 44
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyT

<400> SEQUENCE: 44
aattaccggc aaagagggaa ccagtgagan                              30

<210> SEQ ID NO 45
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyA

<400> SEQUENCE: 45
aacatcagcc ccagagtttg agacaagatn                              30

<210> SEQ ID NO 46
<211> LENGTH: 52
<212> TYPE: DNA
<213> ORGANISM: Homo sapiens

<400> SEQUENCE: 46
ctcactgcta atggggttat gcggttwcaa gggcgtgcat catttcgcac ac     52

<210> SEQ ID NO 47
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyA

<400> SEQUENCE: 47
ctgctcactg ctaatggggt tatgcggttn                              30

<210> SEQ ID NO 48
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyT

<400> SEQUENCE: 48
ctgggtgtgc gaaatgatgc acgcccttgn                              30

<210> SEQ ID NO 49
<211> LENGTH: 30
<212> TYPE: DNA
<213> ORGANISM: Homo sapiens
```

<220> FEATURE:
<221> NAME/KEY: misc_feature
<222> LOCATION: (30)..(30)
<223> OTHER INFORMATION: n is dideoxyT

<400> SEQUENCE: 49
ctgctcactg ctaatggggt tatgcggttn                                      30

<210> SEQ ID NO 50
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyA

<400> SEQUENCE: 50
ctgggtgtgc gaaatgatgc acgcccttgn                                      30

<210> SEQ ID NO 51
<211> LENGTH: 52
<212> TYPE: DNA
<213> ORGANISM: Homo sapiens

<400> SEQUENCE: 51
tgcgtctcgg tccttccttt tcacttwgcc agttgcacat tccctgtcct cc             52

<210> SEQ ID NO 52
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyA

<400> SEQUENCE: 52
tgatgcgtct cggtccttcc ttttcacttn                                      30

<210> SEQ ID NO 53
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyT

<400> SEQUENCE: 53
gtaaggagga cagggaatgt gcaactggcn                                      30

<210> SEQ ID NO 54
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyT

<400> SEQUENCE: 54
tgatgcgtct cggtccttcc ttttcacttn                                      30

<210> SEQ ID NO 55
<211> LENGTH: 30
<212> TYPE: DNA

```
<213> ORGANISM: Homo sapiens
<220> FEATURE:
<221> NAME/KEY: misc_feature
<222> LOCATION: (30)..(30)
<223> OTHER INFORMATION: n is dideoxyA

<400> SEQUENCE: 55
gtaaggagga cagggaatgt gcaactggcn                                    30
```

ULTRA-HIGH SENSITIVE MONITORING OF EARLY TRANSPLANTATION FAILURE

CROSS-REFERENCE TO THE APPLICATION

The present application is a national phase entry under 35 U.S.C. § 371 of PCT/US2012/025393, filed on 16 Feb. 2012, and claims the benefit of priority to U.S. Provisional Application No. 61/445,287, filed 22 Feb. 2011. Each application is incorporated herein by reference in its entirety.

SEQUENCE SUBMISSION

The present application is being filed along with a Sequence Listing in electronic format. The Sequence Listing is entitled 1954548PCTSequenceListing.txt, created on 7 Feb. 2012 and is 11 kb in size. The information in the electronic format of the Sequence Listing is incorporated herein by reference in its entirety.

BACKGROUND OF THE INVENTION

The present invention relates to the field of organ transplantation, more particularly to methods for detecting organ transplantation failure.

The publications and other materials used herein to illuminate the background of the invention, and in particular, cases to provide additional details respecting the practice, are incorporated by reference in their entirety for all that they disclose, and for convenience are referenced in the following text by author and date and are listed alphabetically by author in the appended bibliography.

Transplant Rejection: Transplant rejection occurs when a transplanted organ, tissue, or stem cell is not accepted by the body of the transplant recipient. This is explained by the concept that the immune system of the recipient attacks the transplanted organ or tissue. This is expected to happen, because the immune system's purpose is to distinguish foreign material within the body and attempt to destroy it (http://en.wikipedia.org/wiki/Transplant_rejection).

Although immunosuppressive drugs are used to prevent organ rejection, organ and tissue transplantation would almost always cause an immune response and result in destruction of the foreign tissue. Thus, the dying cells of the foreign tissue releases their DNA and RNA into peripheral blood.

Current Methods in Detection of Transplant Rejection: Currently, transplant rejection can be found by symptoms and signs that the organ isn't functioning properly, such as elevated creatinine or less urine output with kidney transplants, shortness of breath and less tolerance to exertion with heart transplants, and yellow skin color and easy bleeding with liver transplants. A biopsy of the transplanted organ can confirm that it is being rejected. When organ rejection is suspected, one or more of the following tests may be performed prior to organ biopsy, such as abdominal CT scan, chest x-ray, heart echocardiography, kidney arteriography, kidney ultrasound, and lab tests of kidney or liver function. Although the above examinations are available, it is still difficult to detect early stage, particularly very early stage, transplant rejection.

Limits of PCR-Based Technologies: PCR-based methods, such as allele-specific PCR (Newton et al., 1989; Nichols et al., 1989; Sommer et al., 1989; Wu et al., 1989), peptide nucleic acid (PNA) clamping blocker PCR, allele-specific competitive blocker PCR, can typically detect a copy of the point mutation in no more than $10^2$ copies of the wildtype genome, otherwise they cause false positives (Parsons and Heflich, 1997).

In addition to above potential false positives, it is difficult for PCR to detect a single copy of mutations because of primer dimers and false priming sites, causing possible false negatives.

PAP Technology: Pyrophosphorolysis-Activated Polymerization (PAP) is a new nucleic acid amplification technology that has surprising properties for nucleic acid amplification (Liu and Sommer, 2004). For example, its amplification selectivity, or signal to noise ratio, is so extremely high that it can detect a single copy of DNA mutant molecule in 1 billion of almost identical wild type molecules. This level of selectivity is over 1,000,000 times more than that of PCR or any other technologies. In addition, its sensitivity or the detectable smallest copy number of the target molecule can reliably arrive at a single copy level. This level of sensitivity is over 100 times more than that of PCR technology.

It is desired to develop new techniques for monitoring early transplantation failure in transplant donors.

SUMMARY OF THE INVENTION

Transplant rejection occurs when a transplanted organ, tissue, or stem cell is not accepted by the body of the transplant recipient. This is explained by the concept that the immune system or compounds of the recipient attacks the transplanted organ or tissue, which causes donor cells to die and release their DNA into blood. Through detection of minimal levels of donor-positive but recipient-negative DNA markers in recipient's plasma, transplantation failure can be identified at very early stages and therefore therapy can be embarked to patient rejection. In accordance with the present invention, ultra-high sensitive pyrophosphorolysis activated polymerization (PAP) is used to detect even a single copy of donor-positive but recipient-negative DNA markers in recipient blood. Also in accordance with the present invention, a universal set of PAP assays is applied for virtually 100% donors and recipients, such as kidney, liver, heart, lung, islet cell, bone marrow and other transplantations, greatly reducing the cost of monitoring transplantation failure.

Therefore, the present invention has the advantages: i) ability to detect a single copy of the targeted marker in plasma, ii) over 1000-times more sensitive and selective than any current PCR-based methods, iii) constant ratio between the dying cells and the specific marker, iv) cost effective because universal assays can be used, and v) non-invasive testing.

Thus, in one aspect, the present invention provides a method for detecting transplantation failure of a transplanted organ or cells which comprises detecting a donor-positive but recipient-negative DNA marker in the recipient. In one embodiment, one or more donor-positive but recipient-negative DNA markers are detected. In another embodiment, blood or plasma is isolated from the recipient for use in detecting the DNA markers. In an additional embodiment, DNA is isolated from the blood or plasma. In a further embodiment, the presence of the DNA markers is detected using one or more PAP amplification reactions.

In one embodiment, DNA markers that are selected for an individual donor and an individual recipient are used. Such DNA markers are termed individual DNA markers. In another embodiment, DNA markers that are universal for most donors and recipients are used. Such DNA markers are termed universal markers. In a further embodiment, the PAP amplification reactions are used to detect the DNA markers or polymorphisms described herein. In one embodiment, the transplanted organ is heart, liver, lung, kidney, intestine, pancreas, islet cells and bone marrow. In another embodiment, the minimal levels of the DNA markers are detected. Since minimal levels can be detected in accordance with the present invention, early detection of transplantation failure can be detected and treated using appropriate and conventional organ rejection therapy. In accordance with the present invention, any DNA marker or polymorphism that is capable of distinguishing the donor tissue from the recipient tissue can be used to detect early transplantation failure.

In one embodiment, the method comprises a screening step and a tracking step. The screening step comprises screening a donor sample and a recipient sample to identify donor-positive but recipient-negative markers. In one embodiment, the sample may be a plasma sample or it may be any tissue sample. In another embodiment, a set of common biallelic polymorphisms are compared between donor and recipient genomic DNA samples extracted from white blood cells or other tissue samples to select DNA markers that are different between the donor and the recipient. In an additional embodiment, PAP amplification reactions or other well known amplification reactions, such as PCR amplification reactions, can be used for the screening step. The tracking step comprises tracking one or more donor-positive but recipient-negative marker in recipient's blood. In one embodiment, the marker is tracked in recipient's plasma. In another embodiment, a specific PAP assay is performed for detecting the DNA marker(s). Through detection of a DNA marker's presence or increased levels, transplantation failure can be identified at very early stages.

In a second aspect, the present invention provides a method of treating transplantation failure of a transplanted organ or transplanted cells in a subject. In accordance with the present invention, the method comprises (a) detecting transplantation failure in a subject according to the method as disclosed herein and (b) initiating treatment of transplantation failure in the subject if transplantation failure is detected in step (a). Conventional treatments for transplantation failure are well known to the skilled artisan and can be used to treat transplantation failure detected by the present invention.

In a third aspect, the present invention provides a method for detecting transplantation failure of cells that are transplanted in multiple recipients which comprises detecting a donor-positive but recipient-negative DNA marker in the recipient. This method is similar to that described above for the first aspect of the invention with the exception of the markers to be examined and only using a single Bi-Pap assay. In one embodiment, the transplanted cells are engineered stem cells, engineered pluripotent stem cells, differentiated stem cells or differentiated induce pluripotent stem cells. In another embodiment, the blood or plasma is isolated from the recipient for use in detecting the DNA markers. In an additional embodiment, DNA is isolated from the blood or plasma. In a further embodiment, the polymorphism status of the donor is predetermined on many loci by any suitable method, such as Sanger sequencing or parallel sequencing. Homozygous and/or heterozygous genotypes, such as C:G/C:G and/or C:G/G:C of a biallelic polymorphism, are selected for the donor genotypes. To differentiate from the donor genotypes, a genotype, such as a G:C/G:C homozygous genotype, is selected for the recipients. For each such polymorphism locus, the frequencies of C:G allele and G:C allele are accounted in the recipients. High frequency of G:C allele but low frequency of C:G allele are preferred to get the donor-positive but recipient-negative genotypes efficiently.

In a fourth aspect, the present invention provides a method for detecting dying cells of a recipient or cellular damage of a recipient in instances in which cells are transplanted into multiple recipients which comprises detecting a recipient-positive but donor-negative DNA marker in the recipient. This method is similar to that described above for the first aspect of the invention with the exception of the markers to be examined and only using a single Bi-Pap assay. In one embodiment, the transplanted cells are engineered stem cells, engineered pluripotent stem cells, differentiated stem cells or differentiated induce pluripotent stem cells. In another embodiment, the blood or plasma is isolated from the recipient for use in detecting the DNA markers. In an additional embodiment, DNA is isolated from the blood or plasma. In a further embodiment, the polymorphism status of the donor is predetermined on many loci by any suitable method, such as Sanger sequencing or parallel sequencing. Homozygous genotypes, such as G:C/G:C of a biallelic polymorphism, are selected for the donor genotypes. To differentiate from the donor genotypes, genotypes, such as C:G/C:G homozygous genotypes and/or C:G/G:C heterozygous genotypes, are selected for analysis for the recipients. For such an polymorphism locus, the frequencies of C:G allele and G:C allele are also accounted in the recipients. High frequency of C:G allele but low frequency of G:C allele are preferred.

DETAILED DESCRIPTION OF THE INVENTION

Unless defined otherwise, all technical and scientific terms used herein have the same meaning as is commonly understood by one of skill in the art to which the invention belongs.

As used herein, "pyrophosphorolysis activated polymerization" ("PAP") refers to a nucleic acid amplification technology that uses one or more blocked primers and has surprising properties for nucleic acid amplification. In addition to references cited herein, PAP has been described in U.S. Pat. Nos. 6,534,269, 7,033,763, 7,105,298, 7,238,480, 7,504,221, 7,914,995 and 7,919,253, each incorporated herein in their entirety, and in U.S. Patent Application Publication No. 2011/0124051, incorporated herein in its entirety.

As used herein, analytical "sensitivity" refers to the smallest number of copies of a template that generates a detectable product when the blocked primers match the template.

As used herein, analytical "specificity" refers to the largest number of copies of the mismatched template that generates an undetectable product when the blocked primers mismatch the template.

As used herein, analytical "selectivity" refers to the ratio of sensitivity to specificity.

The terms "DNA marker," "DNA polymorphism" or "polymorphism" are used interchangeably herein.

The terms "transplantation failure," "transplant failure," "transplant rejection" or "transplantation rejection" are used interchangeably herein.

Briefly, PAP is based on serial coupling of pyrophosphorolysis and polymerization. Pyrophosphorolysis is the reverse reaction of DNA polymerization in which the 3' nucleotide of a hybridized primer is removed: $[dNMP]_n$+ PPi→$[dNMP]_{n-1}$+dNTP (Deutscher and Kornberg, 1969).

Figure 1:
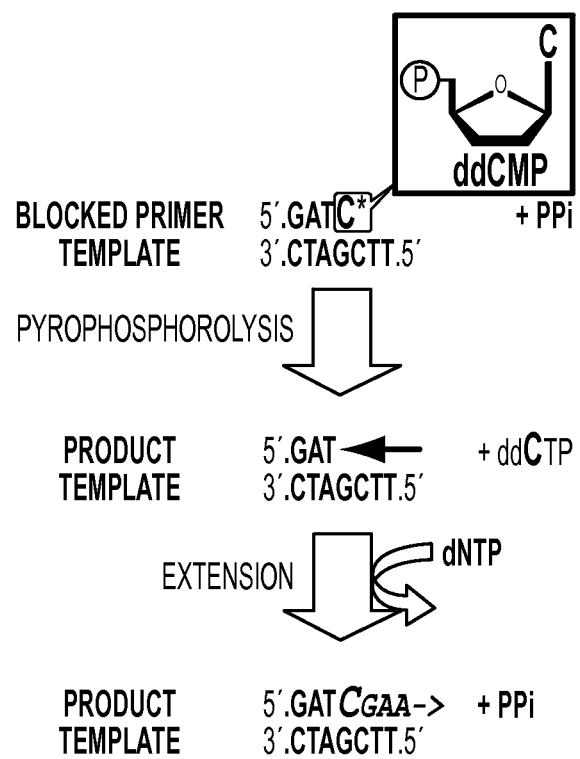
FIG. 1 illustrates the principle of PAP. The primer is blocked at its 3' end with, e.g., a dideoxynucleotide, preventing it from being directly extended. When the blocked primer anneals to its complementary template strand, the 3' blocker can be removed by pyrophosphorolysis. The activated primer can then be extended.

In PAP, the primer (also sometimes referred to as pyrophosphorolysis activatable oligonucleotide (P*)) is blocked at its 3' end preventing it from being directly extended by DNA polymerase (FIG. 1). The 3' end of the primer can be blocked using a 3'deoxynucleotide, a 2',3'-dideoxynucleotide, an acyclonucleotide, 3'-deoxyadenosine (cordycepin), 3'-azido-3'-deoxythymidine (AZT), 2',3'-dideoxyinosine (ddI), 2',3'-dideoxy-3'-thiacytidine (3TC) or 2',3'-didehydro-2',3'-dideoxythymidine (d4T). Alternatively, the primer is an inactive oligonucleotide that is activated by a nucleic acid metabolizing enzyme, such as helicases, topoisomerases, telomerases, RNase H or restriction enzymes. When the blocked primer anneals to its complementary template strand, the 3' blocker can be removed by pyrophosphorolysis. The activated primer can then be extended. In such a way, pyrophosphorolysis and polymerization are serially coupled (Liu and Sommer, 2004). Alternatively, the inactive primer anneals to its complementary template strand, the inactive primer is activated by a nucleic acid metabolizing enzyme. The activated primer can then be extended. In such a way, activation and polymerization are serially coupled (U.S. Pat. No. 7,919,253).

Figure 2:
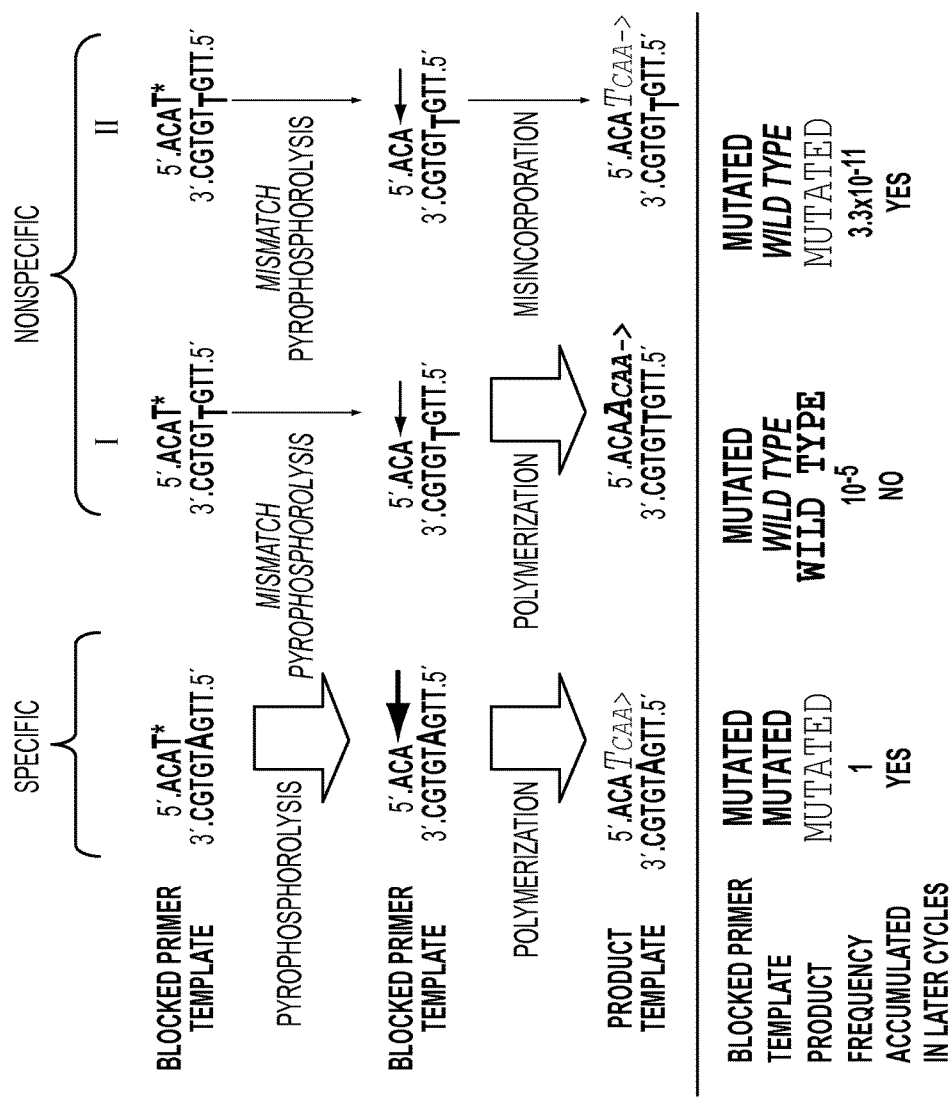
FIG. 2 illustrates that PAP has high selectivity in detecting a mutation in an abundance of the wild type template because of the serial coupling. The blocked primer matches the mutant template and specific amplification occurs efficiently. The blocked primer mismatches the wild type template at the 3' end, causing types I and II nonspecific amplifications. Type I nonspecific amplification occurs rarely when mismatched pyrophosphorolysis occurs (the frequency is estimated to be $10^{-5}$). Type I error cannot be accumulated. Type II error occurs when both mismatched pyrophosphorolysis and mis-incorporation are serially coupled (the coupling frequency is estimated to be $3.3 \times 10^{-11}$) (Kornberg and Baker 1992). Once this Type II error occurs, the mutated product can be accumulated exponentially in subsequent cycles, limiting the selectivity.

The serial coupling provides PAP with extremely high selectivity, because significant nonspecific amplification that causes false positive requires mismatch pyrophosphorolysis followed by mis-incorporation, an event with a frequency estimated to be $3.3 \times 10^{-11}$ (FIG. 2).

The bi-directional form of PAP (Bi-PAP) is especially suitable for allele-specific amplification that uses two opposing blocked primers with one nucleotide overlap at their 3' ends (Liu and Sommer, 2004). Bi-PAP can detect one copy of a mutant allele in the presence of $10^9$ copies of the wildtype DNA with false positives. Briefly, Bi-PAP is a novel design that preferably uses two opposing pyrophosphorolysis activatable oligonucleotides (P*) with one nucleotide overlap at their 3' termini. Thus, in Bi-PAP, PAP is performed with a pair of opposing activatable oligonucleotide P*s. Both the downstream and upstream P*s are specific for the nucleotide of interest at the 3' termini. See, e.g., U.S. Pat. No. 7,033,763.

Figure 3:
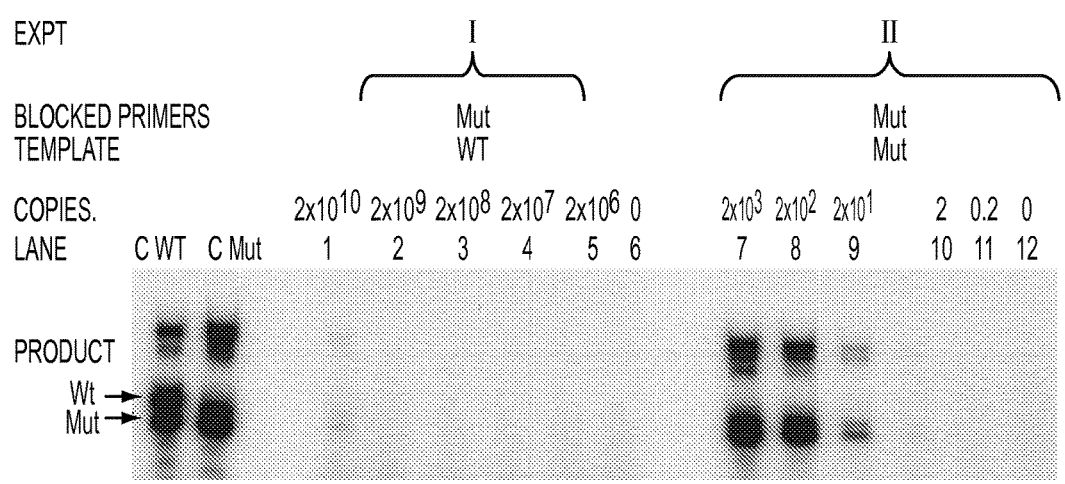
FIG. 3 shows the sensitivity and specificity of Bi-PAP. Experiment I: To test the specificity, the mutant blocked primers mismatched the wildtype DNA template. Only Lane 1 generated the mutant product (false positive). Experiment II: To test the sensitivity, the blocked primers matched the mutant DNA template to generate the mutant product from Lanes 7 to 10. Lane "C WT" is WT control. Lane "C Mut" is Mut control. The WT and Mut products (79 bp) with unique mobility are shown on the left of the non-denaturing PAGE gel.

Using λ phage DNA template, we tested the sensitivity to detect an A:T→T:A mutation when the blocked primers matched the mutant λ phage DNA template (FIG. 3). The smallest number of copies of the matched template with a detectable product, or the sensitivity, is two copies. The specificity was defined when the blocked primers mismatched the wildtype λ phage DNA template at the 3' ends. The largest number of copies of the mismatched template without a detectable product (false positive), or the specificity, is $2 \times 10^9$. The selectivity, the ratio of the sensitivity to the specificity, is thus $1:10^9$. Similar results were also obtained for two other T:A→G:C and T:A→C:G mutations (Liu and Sommer, 2004).

Figure 4A:
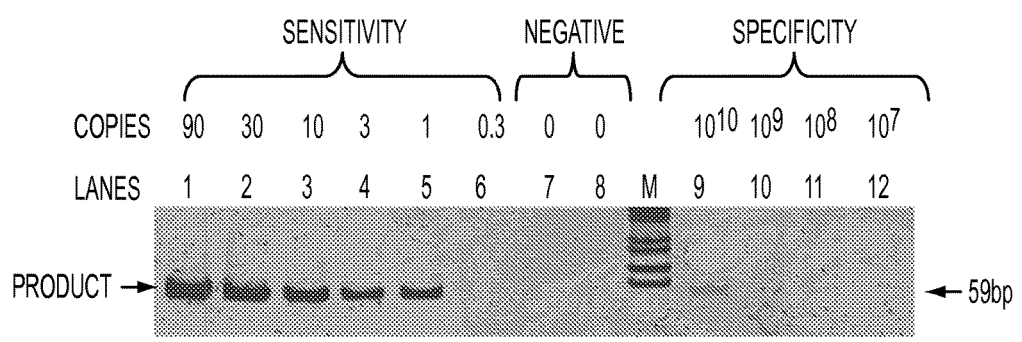
FIGS. 4A and 4B show that Bi-PAP detects an A:T to T:A mutation with high specificity (FIG. 4A), and a C:G to T:A mutation with low specificity (FIG. 4B). In lanes 1 to 6, the sensitivity was examined by a 3-fold serial dilution of the matched mutant template. The sensitivity is one copy. In lanes 9 to 12, the specificity was tested by a 10-fold serial dilution of the mismatched wildtype template. The specificity is $10^9$ copy in (FIG. 4A) and $10^4$ in (FIG. 4B). Lanes 7 and 8 are two negative controls without template. Lane M is 100 ng of Phi-X174/HaeIII DNA.
Figure 4B:
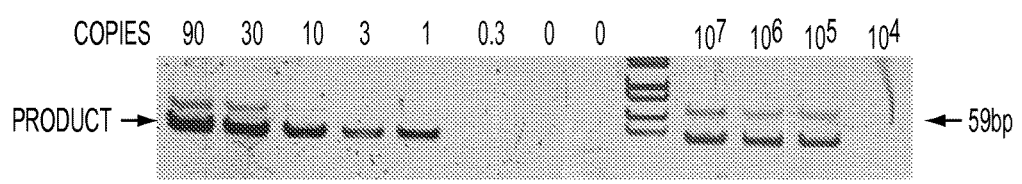

Using human genome, 13 assays targeting all six possible types of single-base substitutions in the P53 gene were further validated (FIG. 4). Twelve assays had sensitivity of one copy and one assay had sensitivity of ten copies of the matched templates (Table 1) (Shi et al., 2007).

TABLE 1

Relationship Between Assay Performance and Mutation Types

| Mutation type[a] | Sensitivity | Specificity | Selectivity | Number of assays |
|---|---|---|---|---|
| A:T→G:C | 1 copy | $10^7$ Copies | $1:10^7$ | 2 |
| A:T→C:G | 10 | $10^9$ | $1:10^8$ | 1 |
| G:C→C:G | 1 | $10^9$ | $1:10^9$ | 3 |
| A:T→T:A | 1 | $10^9$ | $1:10^9$ | 1 |
| G:C→A:T | 1 | $10^4$-$10^5$ | $1:10^4$ to $1:10^5$ | 4 |
| G:C→T:A | 1 | $10^5$-$10^6$ | $1:10^5$ to $1:10^6$ | 2 |

[a]Six possible types of single base substitutions are classified on both sense and antisense stands. For example, G:C→A:T and C:G→T:A are considered as one mutation type.

Two distinct categories of the specificity were recognized, and they were highly associated with the targeted six possible types of single base substitutions. Assays for four types of mutations, A:T→G:C, A:T→C:G, G:C→C:G, and A:T→T:A, had high specificity from $10^7$ to $10^9$, being particularly suitable for the present invention.

Assays for the remaining two types of mutations, G:C→A:T and G:C→T:A, had relatively low specificity between $10^4$ and $10^6$ (Table 1) due to spontaneous damage on the DNA template.

The relatively low specificity and selectivity for G:C→A:T mutation is caused by spontaneous deamination of cytosine, the hydrolysis reaction of dC into dU, or 5'-methylated dC into dT (Frederico et al., 1990).

The relatively low specificity and selectivity for G:C→T:A mutations is due to the presence of 8-oxo-dG in the genomic DNA, which is commonly found in mammalian DNA. DNA polymerases can misincorporate dAMP with 8-oxodG as template (Arif and Gupta, 2003).

However, two types of mutations, G:C→A:T and G:C→T:A, are observed to have lower specificity or selectivity than other types of mutations due to spontaneous chemical damages on DNA template. G:C→A:T mutation is caused by spontaneous deamination of cytosine, the hydrolysis reaction of dC into dU, or 5'-methylated dC into dT. G:C→T:A mutations is due to the spontaneous presence of 8-oxo-dG. Thus, the low specificity is not associated with the PAP inherent property.

In accordance with the present invention, we hypothesized that the level of donor-positive but recipient-negative DNA markers in blood can reflect the status of transplant rejection in early stage because the rejection causes donor cells to die, releasing their DNA into blood. Through detection of minimal levels of donor-positive but recipient-negative DNA markers in recipient's plasma, transplantation failure can be identified at very early stages.

In accordance with the present invention, ultra-high sensitive PAP is used to detect even a single copy of donor-positive but recipient-negative DNA markers in recipient blood. Also importantly, a universal set of PAP assays are applied for virtually 100% donors and recipient including, but not limited to, islet cell, liver, heart, kidney, lung, and bone marrow transplantation, thereby greatly reducing the cost. Therefore, the method of the present invention has the following advantages: i) Ability to detect a single copy of the targeted marker in plasma, ii) Over 1000-times more sensitive and selective than any current PCR-based methods, iii) constant ratio between the dying cells and the specific marker, iv) Cost effective because of universal assays, and v) Non-invasive testing.

Thus, in one aspect, the present invention provides a method for detecting transplantation failure of a transplanted organ or cells which comprises detecting a donor-positive but recipient-negative DNA marker in the recipient's plasma. In one embodiment, one or more donor-positive but recipient-negative DNA markers are detected. In another embodiment, plasma is isolated from the recipient for use in detecting the DNA markers. In an additional embodiment, DNA is isolated from the plasma. In a further embodiment, the presence of the DNA markers is detected using one or more PAP amplification reactions, preferably one or more Bi-PAP amplification reactions.

In one embodiment, DNA markers that are selected for an individual donor and an individual recipient are used. Such DNA markers are termed individual DNA markers. In one embodiment, DNA markers are screened with respect to the individual donor and the individual recipient to identify one or more suitable DNA markers that can be used to track transplantation failure in the donor. In one embodiment, suitable DNA markers that can be screened include HLA alleles.

In another embodiment, DNA markers that are universal for most donors and recipients are used. Such DNA markers are termed universal markers. In one embodiment, the universal DNA markers or polymorphisms are single nucleotide polymorphisms. In accordance with the present invention, factors which are used to guide polymorphism selection include (i) polymorphism reliability, (ii) polymorphism type and (iii) polymorphism frequency. With respect to polymorphism reliability, only well validated polymorphisms are used. Well validated polymorphisms include, but are not limited to, HapMap, CEPH, AFD, and the like. With respect to polymorphism type, only C/G, G/C, T/A and A/T polymorphisms are used in order to avoid issues of spontaneous DNA damage taking place that can occur with C/T, G/A, T/C and G/A polymorphisms. With respect to polymorphism frequency, it is preferred to use polymorphisms having a frequency of greater than or equal to about 30% and less than or equal to about 70%, preferably a frequency of about 50%. Polymorphisms with this frequency are preferred in order to minimize the number of polymorphisms that are needed to test nearly 100% of donors and recipients. In accordance with the present invention, it has been found that 11 polymorphisms can be selected for use in the method of the present invention to cover nearly 100% of all transplantation cases. It is evident that more polymorphisms can be developed and used if it is desired, or if none of the 11 polymorphisms is capable of distinguishing between the donor and the recipient. The selected polymorphisms are sometimes termed a polymorphism panel herein. In a further embodiment, the PAP amplification reactions are used to detect the polymorphisms described herein.

In one embodiment, the transplanted organ is heart, liver, lung, kidney, intestine, pancreas, islet cells and bone marrow. In another embodiment, the minimal levels of the DNA markers are detected. Since minimal levels can be detected in accordance with the present invention, early detection of transplantation failure can be detected and treated using appropriate and conventional organ rejection therapy. In accordance with the present invention, any DNA marker or polymorphism that is capable of distinguishing the donor tissue from the recipient tissue can be used to detect early transplantation failure.

In one embodiment, the method comprises a screening step and a tracking step. The screening step comprises screening a donor sample and a recipient sample to identify donor-positive but recipient-negative markers. In one embodiment, the sample may be a plasma sample or it may be any tissue sample. In another embodiment, a set of common biallelic polymorphisms are compared between donor and recipient genomic DNA samples extracted from white blood cells or other tissue samples to select DNA markers that are different between the donor and the recipient. In an additional embodiment, PAP amplification reactions or other well known amplification reactions, such as PCR amplification reactions, can be used for the screening step. The tracking step comprises tracking one or more donor-positive but recipient-negative marker in recipient's blood over a desired period of time, e.g., daily, every other day, semi-weekly, weekly, etc., to detect the presence or increased levels of the marker as an indicator of transplantation failure. In one embodiment, the marker is tracked in recipient's plasma. In another embodiment, a specific PAP assay is performed for detecting the DNA marker(s). Through detection of a DNA marker's presence or increased levels, transplantation failure can be identified at very early stages, and appropriate treatment can be initiated at an earlier time.

In a second aspect, the present invention provides a method of treating transplantation failure of a transplanted organ or transplanted cells in a subject. In accordance with the present invention, the method comprises (a) detecting transplantation failure in a subject according to the method as disclosed herein and (b) initiating treatment of transplantation failure in the subject if transplantation failure is detected in step (a). Conventional treatments for transplantation failure are well known to the skilled artisan and can be used to treat transplantation failure detected by the present invention.

In a third aspect, the present invention provides a method for detecting transplantation failure of cells that are transplanted in multiple recipients which comprises detecting a donor-positive but recipient-negative DNA marker in the recipient. This method is similar to that described above for the first aspect of the invention with the exception of the markers to be examined and only using a single Bi-Pap assay. In one embodiment, the transplanted cells are engineered stem cells, engineered pluripotent stem cells, differentiated stem cells or differentiated induce pluripotent stem cells. In another embodiment, the blood or plasma is isolated from the recipient for use in detecting the DNA markers. In an additional embodiment, DNA is isolated from the blood or plasma. In a further embodiment, the polymorphism status of the donor is predetermined on many loci by any suitable method, such as Sanger sequencing or parallel sequencing. Homozygous and/or heterozygous genotypes, such as C:G/C:G and/or C:G/G:C of a biallelic polymorphism, are selected for the donor genotypes. To differentiate from the donor genotypes, a genotype, such as a G:C/G:C homozygous genotype, is selected for the recipients. For each such polymorphism locus, the frequencies of C:G allele and G:C allele are accounted in the recipients. High frequency of G:C allele but low frequency of C:G allele are preferred to get the donor-positive but recipient-negative genotypes efficiently.

In a fourth aspect, the present invention provides a method for detecting dying cells of a recipient or cellular damage of a recipient in instances in which cells are transplanted into multiple recipients which comprises detecting a recipient-positive but donor-negative DNA marker in the recipient. This method is similar to that described above for the first aspect of the invention with the exception of the markers to be examined and only using a single Bi-Pap assay. In one embodiment, the transplanted cells are engineered stem cells, engineered pluripotent stem cells, differentiated stem cells or differentiated induce pluripotent stem cells. In another embodiment, the blood or plasma is isolated from the recipient for use in detecting the DNA markers. In an additional embodiment, DNA is isolated from the blood or plasma. In a further embodiment, the polymorphism status of the donor is predetermined on many loci by any suitable method, such as Sanger sequencing or parallel sequencing. Homozygous genotypes, such as G:C/G:C of a biallelic polymorphism, are selected for the donor genotypes. To differentiate from the donor genotypes, genotypes, such as C:G/C:G homozygous genotypes and/or C:G/G:C heterozygous genotypes, are selected for analysis for the recipients. For such an polymorphism locus, the frequencies of C:G allele and G:C allele are also accounted in the recipients. High frequency of C:G allele but low frequency of G:C allele are preferred.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, New York); Sambrook et al., 1989, *Molecular Cloning*, 2nd Ed. (Cold Spring Harbor Laboratory Press, Cold Spring Harbor, New York); Sambrook and Russell, 2001, *Molecular Cloning*, 3rd Ed. (Cold Spring Harbor Laboratory Press, Cold Spring Harbor, New York); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, New York); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which is offered by way of illustration and is not intended to limit the invention in any manner.

Standard techniques well known in the art or the techniques specifically described below were utilized.

Example 1

Materials and Methods

Separation of Plasma from Cells: 10 mL of peripheral blood was collected in an EDTA anticoagulation tube and then centrifuged at 1,300 RCF (2,500 rpm with CAT 218 swing rotor, Forma Scientific) for 10 min at 4° C. Remove plasma in the upper layer into 1.5 mL Eppendorf tubes. About 5 mL of plasma was collected from each EDTA tube. The white and red cells in the lower layer was re-suspended in PBS buffer.

Extraction of Plasma DNA for Tracking: Plasma DNA was extracted using Qiamp MinElute Virus Spin Kit (Qiagen Cat 57704) according to manufacture's instruction. 1 mL of plasma was processed and 45 μL of plasma DNA was finally eluted to an 1.5 mL Eppedorf tube with an estimated recovery efficiency of 90%.

Two revisions were made to the standard protocol: 1) the elution buffer contains 10 mM Tris/HCl, pH 8.0, 0.1 mm EDTA for convenience in downstream treatment; and 2) the elution buffer was heated to 70° C. before its use for high recovery efficiency.

Extraction of Cellular DNA for Screening: The cellular DNA was extracted using QIAamp Blood kit according to manufacturer's protocol (Qiagen). The resulting DNA was separately resolved in 50 μL of TE buffer.

Preparation of Standard Genomic DNA Pool: To get the expected frequency of the polymorphisms, 16 genomic DNA samples extracted from 16 Caucasians were pooled with equal quantity. To simulate the size of plasma DNA in vivo, the genomic DNA was randomly sheared to about 150-200 bp by an ultrasonic instrument and then extracted by a Qiagen DNA extraction kit.

Bi-PAP Assays: The blocked primers (Table 2) were purchased from BioVision USA. The PAP reaction mixture will contain 800 mM Tris HCl (pH 7.8 at 25° C.), 10 mM $(NH_4)_2SO_4$, 1.0 mM $MgCl_2$, 25 μM each dNTP, 0.1 μM each blocked primer, 90 μM $Na_4PPi$, 2 U of PAPase DNA polymerase (BioVision, USA), 0.1× Sybr Green I, and genomic DNA template in 25 μL of reaction (10 μL of plasma DNA sample was typically used, equivalent to 200 μL of plasma).

TABLE 2

Primer Design for C:G/G:C and A:T/T:A Polymorphisms

| NAME | CH | SEQUENCE (SEQ ID NO:) | C% | G% | GC% |
|---|---|---|---|---|---|
| Rs396 | 5p | 5'ACACAGTGCCCTTCTTGCAAGTACTA[C/G]GACACTCCAATCCCATTTCTACCTC (1) | 50 | 50 | |
| #6-D-1 | | 5'GGCACACAGTGCCCTTCTTGCAAGTACTAddC (2) | For C allele | | 53 |
| #6-U-1 | | 5'CCCTGAGGTAGAAATGGGATTGGAGTGTCddG (3) | | | 53 |
| #6-D-2 | | 5'GGCACACAGTGCCCTTCTTGCAAGTACTAddG (4) | For G allele | | 53 |
| #6-U-2 | | 5'CCCTGAGGTAGAAATGGGATTGGAGTGTCddC (5) | | | 53 |
| | | | | | |
| Rs7289 | 1q | 5'CACTGGACCTTACAGTTCTCACTGCC[C/G]TTGGACTCCAGTCCAGCTTTGGGGC (6) | 49.2 | 51.8 | |
| #13-D-1 | | 5'CTTCACTGGACCTTACAGTTCTCACTGCCddC (7) | For C allele | | 53 |
| #13-U-1 | | 5'CCCAGCCCCAAAGCTGGACTGGAGTCCAAddG (8) | | | 63 |
| #13-D-2 | | 5'CTTCACTGGACCTTACAGTTCTCACTGCCddG (9) | For G allele | | 53 |
| #13-U-2 | | 5'CCCAGCCCCAAAGCTGGACTGGAGTCCAAddC (10) | | | 63 |
| | | | | | |
| Rs7825 | 1p | 5'TGACACCAGAGGGGCTTAGGCTTCTT[C/G]ATCCACAGCAGAGTTTTCTGGGATT (11) | 49.2 | 50.8 | |
| #4-D-1 | | 5'TTCTGACACCAGAGGGGCTTAGGCTTCTTddC (12) | For C allele | | 53 |
| #4-U-1 | | 5'AAGAAATCCCAGAAAACTCTGCTGTGGATddG (13) | | | 43 |
| #4-D-2 | | 5'TTCTGACACCAGAGGGGCTTAGGCTTCTTddG (14) | For G allele | | 53 |
| #4-U-2 | | 5'AAGAAATCCCAGAAAACTCTGCTGTGGATddC (15) | | | 43 |
| | | | | | |
| Rs11793 | 1q | 5'TCCCAAGAACACCTACTAATTCCTCT[C/G]CACTCCTTCATGGCTGGGACAGTTA (16) | 50 | 50 | |
| #5-D-1 | | 5'CGGTCCCAAGAACACCTACTAATTCCTCTddC (17) | For C allele | | 50 |
| #5-U-1 | | 5'CCAGTAACTGTCCCAGCCATGAAGGAGTGddG (18) | | | 56 |
| #5-D-2 | | 5'CGGTCCCAAGAACACCTACTAATTCCTCTddG (19) | For G allele | | 50 |
| #5-U-2 | | 5'CCAGTAACTGTCCCAGCCATGAAGGAGTGddC (20) | | | 56 |
| | | | | | |
| Rs11901 | 16p or q | 5'GCCCTCCTTTCCCAGTCCAAGGTTGA[C/G]AGGGTCCTGTCATTTCCTGTCCCAA (21) | 47.5 | 52.5 | |
| #3-D-1 | | 5'GAAGCCCTCCTTTCCCAGTCCAAGGTTGAddC (22) | For C allele | | 53 |
| #3-U-1 | | 5'CTACTTGGGACAGGAAATGACAGGACCCTddG (23) | | | 57 |
| #3-D-2 | | 5'GAAGCCCTCCTTTCCCAGTCCAAGGTTGAddG (24) | For G allele | | 53 |
| #3-U-2 | | 5'CTACTTGGGACAGGAAATGACAGGACCCTddC (25) | | | 57 |
| | | | | | |
| Rs33296 | 5q | 5'GTACTTTTTGGCATGTACTCTCCACG[C/G]CATAATTTGTAAATGCCCTGGTCTT (26) | 49.2 | 50.8 | |
| #2-D-1 | | 5'TATGTACTTTTTGGCATGTACTCTCCACGddC (27) | For C allele | | 43 |
| #2-U-1 | | 5'CCGCAAGACCAGGGCATTTACAAATTATGddG 28( ) | | | 47 |
| #2-D-2 | | 5'TATGTACTTTTTGGCATGTACTCTCCACGddG (29) | For G allele | | 43 |
| #2-U-2 | | 5'CCGCAAGACCAGGGCATTTACAAATTATGddC (30) | | | 47 |
| | | | | | |
| Rs153887 | 5q | 5'CCAAGGGGAATTTCAGTGCAGGATGT[C/G]TTGTGATGGGAGTAGTGAGTTAGCA (31) | 50.9 | 49.1 | |
| #1-D-1 | | 5'ATACCAAGGGGAATTTCAGTGCAGGATGTddC (32) | For C allele | | 43 |
| #1-U-1 | | 5'CAAATGCTAACTCACTACTCCCATCACCAAddG (33) | | | 46 |
| #1-D-2 | | 5'ATACCAAGGGGAATTTCAGTGCAGGATGTddG (34) | For G allele | | 43 |
| #1-U-2 | | 5'CAAATGCTAACTCACTACTCCCATCACCAAddC (35) | | | 46 |
| | | | | | |
| Rs4261 | 7q | 5'TAAAATTATCCCTGGGCTCTCAGTAA[A/T]GCCAATTGATGTCATCACTTGGACA (36) | 50.8 | 49.2 | |
| #7-D-1 | | 5'GGCTAAAATTATCCCTGGGCTCTCAGTAAddA (37) | For A allele | | 43 |
| #7-U-1 | | 5'ACACTGTCCAAGTGATGACATCAATTGGCddT (38) | | | 43 |

TABLE 2-continued

Primer Design for C:G/G:C and A:T/T:A Polymorphisms

| NAME | CH | SEQUENCE (SEQ ID NO:) | C% | G% | GC% |
|---|---|---|---|---|---|
| #7-D-2 | | 5'GGCTAAAATTATCCCTGGGCTCTCAGTAAddT (39) | For T allele | | 43 |
| #7-U-2 | | 5'ACACTGTCCAAGTGATGACATCAATTGGCddA (40) | | | 43 |
| Rs30209 | 16p | 5'TACCGGCAAAGAGGGAACCAGTGAGA[A/T]ATCTTGTCTCAAACTCTGGGGCTGA (41) | 45.8 | 54.2 | |
| #8-D-1 | | 5'AATTACCGGCAAAGAGGGAACCAGTGAGAddA (42) | For A allele | | 47 |
| #8-U-1 | | 5'AACATCAGCCCCAGAGTTTGAGACAAGATddT (42) | | | 43 |
| #8-D-2 | | 5'AATTACCGGCAAAGAGGGAACCAGTGAGAddT (44) | For T allele | | 47 |
| #8-U-2 | | 5'AACATCAGCCCCAGAGTTTGAGACAAGATddA (45) | | | 43 |
| Rs31224 | 5q | 5'CTCACTGCTAATGGGGTTATGCGGTT[A/T]CAAGGGCGTGCATCATTTCGCACAC (46) | 46.6 | 53.4 | |
| #9-D-1 | | 5'CTGCTCACTGCTAATGGGGTTATGCGGTTddA (47) | For A allele | | 50 |
| #9-U-1 | | 5'CTGGGTGTGCGAAATGATGCACGCCCTTGddT (48) | | | 57 |
| #9-D-2 | | 5'CTGCTCACTGCTAATGGGGTTATGCGGTTddT (49) | For T allele | | 50 |
| #9-U-2 | | 5'CTGGGTGTGCGAAATGATGCACGCCCTTGddA (50) | | | 57 |
| Rs156988 | 1p tel | 5'TGCGTCTCGGTCCTTCCTTTTCACTT[A/T]GCCAGTTGCACATTCCCTGTCCTCC (51) | 54.2 | 45.8 | |
| #12-D-1 | | 5'TGATGCGTCTCGGTCCTTCCTTTTCACTTddA (52) | For A allele | | 47 |
| #12-U-1 | | 5'GTAAGGAGGACAGGGAATGTGCAACTGGCddT (53) | | | 53 |
| #12-D-2 | | 5'TGATGCGTCTCGGTCCTTCCTTTTCACTTddT (54) | For T allele | | 47 |
| #12-U-2 | | 5'GTAAGGAGGACAGGGAATGTGCAACTGGCddA (55) | | | 53 | tel = telomer

The cycling conditions were 30 cycles for screening and 40 cycles for tracking: 95° C. for 15 s, 60° C. for 30 s, 64° C. for 30 s, 68° C. for 1 min, and 72° C. for 1 min. A denaturing step of 95° C. for 2 min was added before the first cycle.

A Bio-Rad CFX96 real time PCR detection system was used with Sybr Green fluorophore for real time detection of the amplified product. Threshold cycle (Ct) was obtained and fluorescence signal was quantified with baseline subtracted mode.

In addition for confirmation, the product was electrophoresed through a standard 3% agarose gel. The gel was stained with ethidium bromide for UV photography by a charge-coupled device camera.

Example 2

A Two-Step Procedure of Screening and Tracking

Figure 5:
FIG. 5 shows a two-step procedure of screening and tracking in accordance with one embodiment of the present invention.
Figure 5:
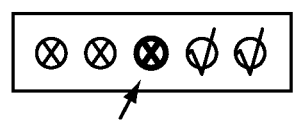
Figure 5:
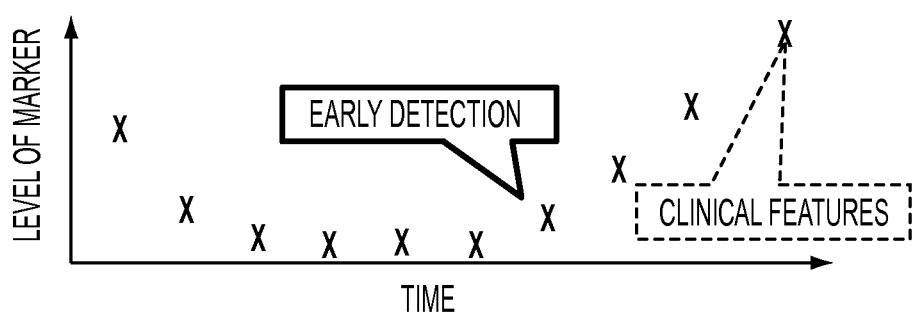

In the first step for screening for donor-positive but recipient-negative markers, a set of common biallelic polymorphisms are compared between donor and recipient genomic DNA samples extracted from white blood cells or other tissue samples (FIG. 5). PAP assays or other methods may be applied.

In the second step, for tracking of a donor-positive but recipient-negative marker in recipient's blood, such as plasma DNA, a specific PAP assay is performed. Through detection of its presence or increased levels, transplantation failure can be identified at very early stages (FIG. 5).

Example 3

Individual Assays Vs. Universal Assays

Individual assays mean that each individual pair of donor and recipient needs a specific assay for them selves. For example, we can identify HLA variances between the specific donor and recipient, and then develop an individualized PAP assay. The disadvantage is that this assay could not be used for others.

Universal assays mean that a set of assays can be applied for most, if not all, the donors and recipients. Common biallelic polymorphisms can be chosen for this purpose. Universal assays are preferred because of their broad utility and low cost.

Example 4

Frequency of Biallelic DNA Polymorphisms

For each biallelic polymorphism locus, such as C:G/G:C, two Bi-PAP assays can be developed. The frequency of biallelic polymorphisms affects the power to identify a donor-positive but recipient-negative polymorphism (Table 3). With 50% biallelic frequency, one PAP assay has 18.75% chance to identify a donor-positive but recipient-negative marker, and 2 assays for the locus has 37.5% such chance, higher than with other frequencies. Thus, biallelic polymorphisms with about 50% frequency were chosen (Table 2).

TABLE 3

Frequency Power for a Donor-Positive but Recipient-Negative Biallelic Polymorphism

| | Positive donor genotype | Negative recipient genotype | | Joint frequency |
|---|---|---|---|---|
| A. Biallele frequency with C:G = 50%, G:C = 50% | | | | |
| Assay I for C:G allele | C:G and C:G 25% | C:G and G:C 50% | G:C and G:C 25% | 18.75% |
| Assay II for G:C allele | G:C and G:C 25% | C:G and G:C 50% | C:G and C:G 25% | 18.75% |
| B. Biallele frequency with C:G = 30%, G:C = 70% | | | | |
| Assay I for C:G allele | C:G and C:G 9% | C:G and G:C 42% | GC and G:C 49% | 24.99% |
| Assay II for G:C allele | G:C and G:C 49% | C:G and G:C 42% | C:G and C:G 9% | 8.19% |

For example, 11 common biallelic polymorphisms can be chosen to develop 22 corresponding PAP assays that can identify at least one donor-positive but recipient-negative polymorphism in virtually 100% of donors and recipients.

Example 5

Types of Biallelic DNA Polymorphisms as Markers

There are 6 possible types of mutations of A:T→G:C, A:T→C:G, G:C→C:G, A:T→T:A, G:C→A:T and G:C→T:A. Bi-PAP assays had ultrahigh selectivity for 4 types of mutations of A:T→G:C, A:T→C:G, G:C→C:G, and A:T→T:A, (Shi et al. 2007). Assays for the remaining two types of mutations of G:C→A:T and G:C→T:A, had relatively low selectivity due to spontaneous damage on the DNA template, such as spontaneous deamination of cytosine (Frederico et al., 1990).

Corresponding, there are only 4 possible types of biallelic polymorphisms of A:T/G:C, A:T/C:G, G:C/C:G, and A:T/T:A. Bi-PAP assays had ultrahigh selectivity for 2 types of biallelic polymorphisms of G:C/C:G and A:T/T:A. Therefore, G:C/C:G and A:T/T:A polymorphisms are of choice for the present invention.

Example 6

Development of Bi-PAP Assay

Figure 6:
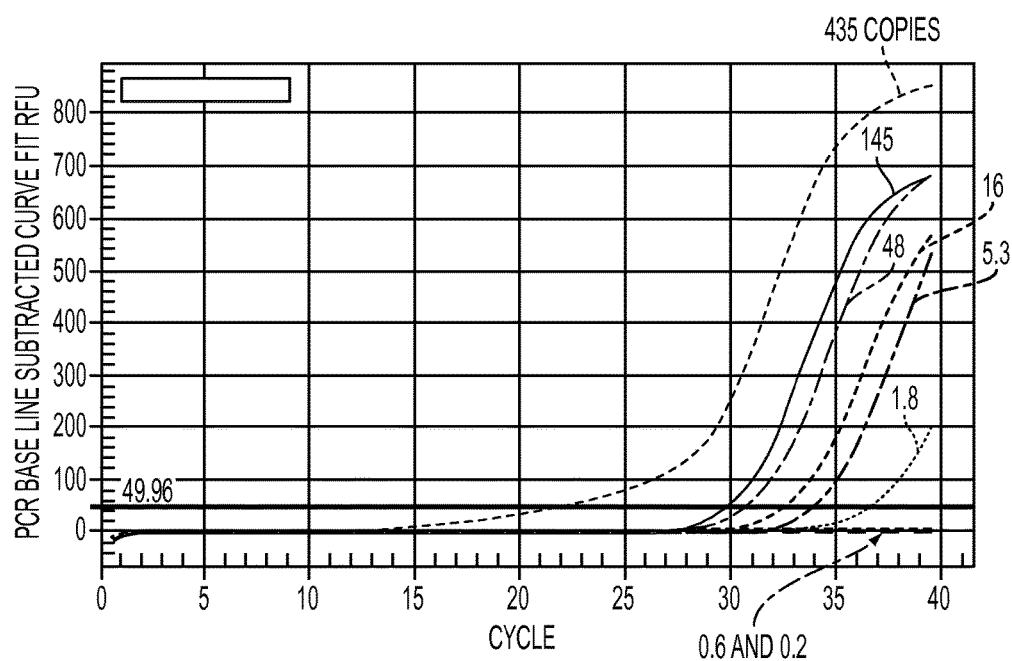
FIG. 6 shows a typical real time PAP sensitivity with matched template. Assay 3 is exampled. Pooled standard genomic DNA was 3-fold serially diluted with the matched copied indicated.

Eleven G:C/C:G and A:T/T:A biallelic polymorphisms were chosen (Table 2). For each biallelic polymorphism, two corresponding Bi-PAP assays were developed and validated. To test the analytical sensitivity of an assay, the matched pooled DNA template was 3-fold titrated from ~435 copies to 1 copy per reaction. We demonstrated the detection of as few as 1 copy of the DNA template (sensitivity=1 copy). In addition, a standard curved was constructed with 3-fold serial dilution from 435 copies to less than 1 copy per reaction. Due to random sampling, the actual copy number per reaction is a random variety estimated by the Poisson distribution. For example, if the expected copy number is one per reaction, 37% of reactions are expected to contain zero copies and 63% are expected to contain one or more copies. If 3 copies are expected per reaction, at least 1 actual copy is included in 95% chance. Threshold cycle (Ct) was typically correlated to copies with 0.97 to 1.07 amplification efficiency, 0.98 to 0.99 $R^2$, and −3.13 to −3.17 slope, showing highly consistent and linear (FIG. 6).

To test the analytical specificity, the blocked primers mismatch the DNA template at their 3' ends. Up to $3 \times 10^5$ copies, or 1 μg, of the mismatched genomic DNA template was applied repeatedly without any false positive signal by the end of 40 cycles (specificity $\geq 10^6$). Furthermore, no template control was also tested without any false positive signal by the end of 40 cycles.

Figure 7:
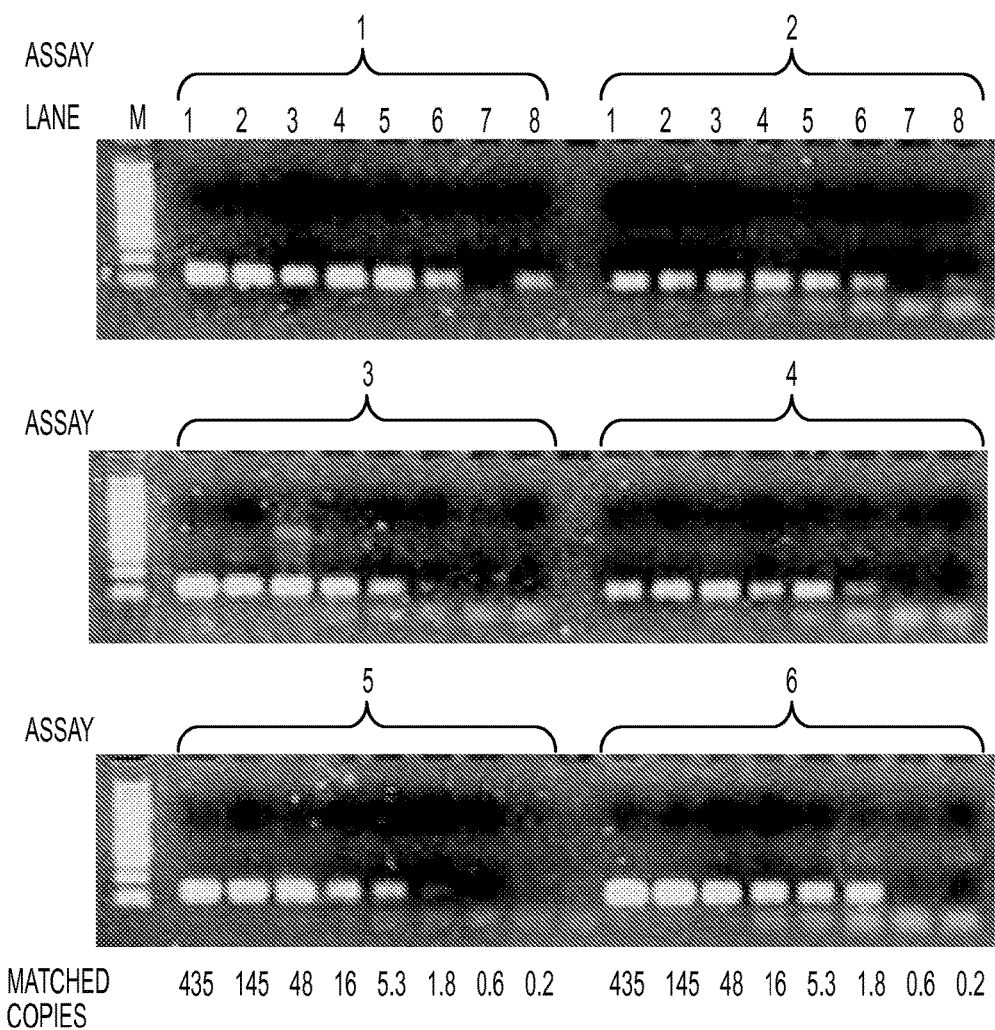
FIG. 7 shows PAP sensitivity with matched template on agarose gel. Assays 1 to 6 are shown. Lane M is 100 ng of Phi-X174/HaeIII DNA.
Figure 8A:
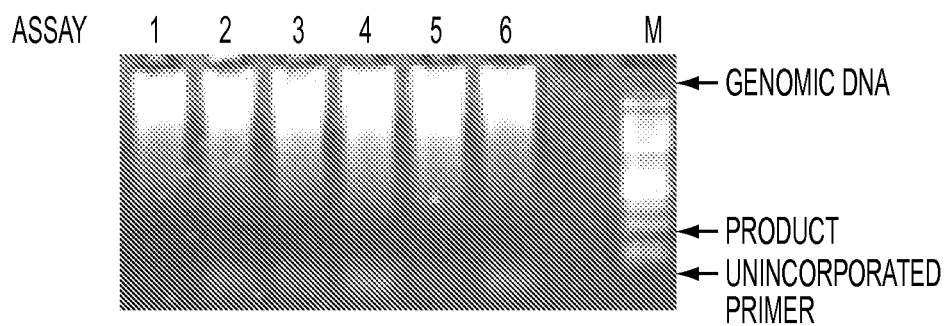
FIGS. 8A and 8b show PAP specificity with mismatched genomic DNA template (FIG. 8A) and no DNA (FIG. 8B) on agarose gel. Assays 1 to 6 are shown.
Figure 8B:
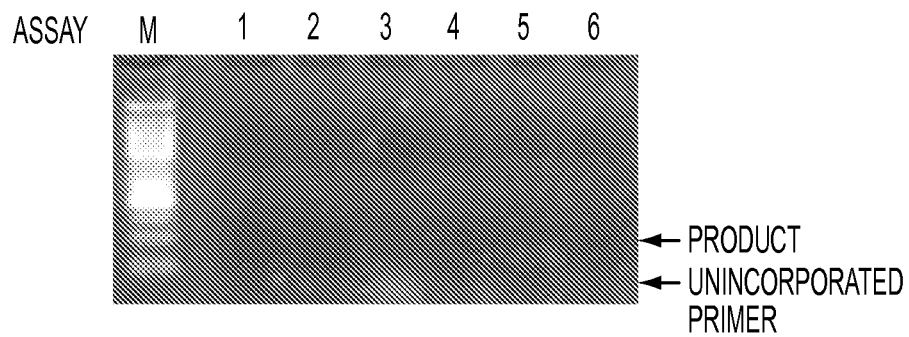

Besides real time detection of the amplified product, the product was analyzed on 3% agarose gel for confirmation of the sensitivity (FIG. 7) and specificity (FIG. 8).

Example 7

Example of Clinical Validation of Islet Transplantation

After a set of PAP assays were developed for 11 common polymorphisms (Table 2) and validated in real-time fluorescence detection format (SybrGreen dye), analysis of 15 islet transplantation patients were conducted.

As the first step (FIG. 5), we genotyped the donor and recipient genomic DNA isolated from their white blood cells and even formalin-fixed tissues. With the 11 common polymorphisms, at least one donor-positive but recipient-negative DNA markers were identified in more than 93% of cases (14 out of 15).

Figure 9:
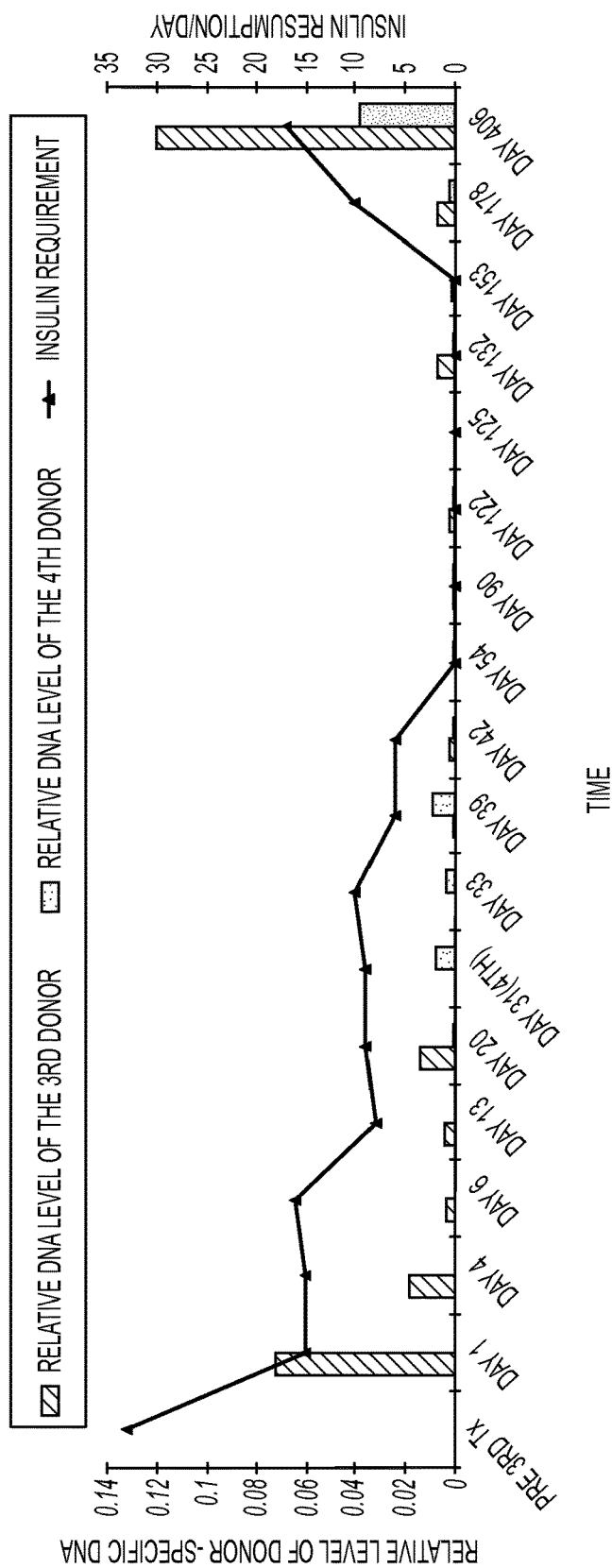
FIG. 9 shows monitoring islet cell transplantation rejection through detection of donor-positive but recipient-negative DNA markers in recipient's plasma. The patient received the third and fourth islet cell transplantations. During post transplantation, the patient showed levels of donor-positive but recipient-negative DNA markers in plasma. Importantly, a strong second peak of donor-positive but recipient-negative DNA markers occurred around the time when Insulin resumption was greatly increased together with higher Cylex and immuno-suppresive drug levels, suggesting a graft rejection. A PAP assay was used to measure the absolute copy number of donor-positive but recipient-negative DNA markers in 1 mL of plasma and then converted to the relative level to the total amount of plasma DNA.

As the second step (FIG. 5), we monitored such donor-positive but recipient-negative DNA markers in recipient's plasma. Two types of increased levels or peaks of donor-positive but recipient-negative markers were detected. The first peak in each patient started directly after islet infusion and lasted for a mean of 22 days (15-28). The second peak was observed in follow-up period in 80% of cases that was associated with islet graft injury as suggested by more insulin requirement, blood glucose excursion, or more immunosuppressive drug requirement, demonstrating the feasibility. An example is shown in FIG. 9.

Example 8

Example of Clinical Validation of Bone Marrow Transplantation

Samples from 6 pair of recipients and donors collected before and after bone marrow transplantation were analyzed. As the first step (FIG. 5), we genotyped the donor and recipient genomic DNA isolated from their nuclear cells, such as white blood cells. With the common polymorphisms and corresponding assays, 1 to 6 donor-positive but recipient-negative DNA markers were identified for each of the 6 pair of recipients and donors.

As the second step (FIG. 5), we identified such donor-positive but recipient-negative DNA markers in 5 out of 6 recipient's plasma collected in post-transplantation with low to medium levels of the markers detected, proving the principle. The one negative result of the donor-positive but recipient-negative DNA marker is presumed due to degradation of plasma DNA in sample storage.

Example 9

Allele Frequency of DNA Polymorphisms for One-Donor Vs. Multiple-Recipients

There is another case where a large volume of cells from one donor is provided to many recipients, such as engineered stem cells. In such a case, another strategy as described din this example can be used efficiently for detecting donor-positive but recipient-negative genotypes in recipient's blood.

For the donor, the polymorphism status is predetermined on many loci by such methods as Sanger sequencing or parallel sequencing. Then homozygous and/or heterozygous genotypes, such as C:G/C:G and/or C:G/G:C of a biallelic polymorphism, are selected. To differentiate from the donor genotypes, a G:C/G:C homozygous genotype is used for the recipients.

For such an polymorphism locus, the frequencies of C:G allele and G:C allele are accounted in the recipients. High frequency of G:C allele but low frequency of C:G allele are preferred to get the donor-positive but recipient-negative genotypes efficiently (Table 4). In addition, one Bi-PAP assay rather than two Bi-PAP assays is applied to each polymorphism.

TABLE 4

Frequency Power for a Donor-Positive but Recipient-Negative
Biallelic Polymorphism with the Donor's Genotypes Predetermined

|  | Positive donor genotype Predetermined | Negative recipient genotype | Joint frequency |
|---|---|---|---|
| A. Biallele frequency with C:G = 30%, G:C = 70% | | | |
| Assay I for C:G allele | C:G and C:G | C:G and G:C | G:C and G:C 49% | 49% |
| B. Biallele frequency with C:G = 50%, G:C = 50% | | | |
| Assay I for C:G allele | C:G and C:G | C:G and G:C | G:C and G:C 25% | 25% |
| C. Biallele frequency with C:G = 70%, G:C = 30% | | | |
| Assay I for C:G allele | C:G and C:G | C:G and G:C | G:C and G:C 9% | 9% |

In addition, it may be desirable to determine if recipient cells are dying are if there is cellular damage of the recipient. In this instance, recipient-positive but donor-negative genotypes in recipient's blood are detected. For example, the donor has predetermined G:C/G:C homozygous genotypes of a biallelic polymorphism. Then, the recipients C:G/C:G homozygous genotypes and/or C:G/G:C heterozygous genotypes are selected for analysis. For such an polymorphism locus, the frequencies of C:G allele and G:C allele are also accounted in the recipients. High frequency of C:G allele but low frequency of G:C allele are preferred. In addition, one Bi-PAP assay rather than two Bi-PAP assays is applied to each polymorphism.

In the description of the invention, it is understood that the use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Arif, J. M. and, Gupta, R. C. (2003). Artifactual formation of 8-oxo-2'-deoxyguanosine: role of fluorescent light and inhibitors. *Oncology Reports* 10(6):2071-2074.

Deutscher, M. P. and Kornberg, A. (1969). Enzymatic synthesis of deoxyribonucleic acid. 28. The pyrophosphate exchange and pyrophosphorolysis reactions of deoxyribonucleic acid polymerase. *Journal Biol Chem* 244(11):3019-3028.

Frederico, L. A. et al. (1990). A sensitive genetic assay for the detection of cytosine deamination: determination of rate constants and the activation energy. *Biochem* 29(10):2532-2537.

Kornberg, A. and Baker, T. A. (1992). *DNA Replication*. Second Edition, W.H. Freeman and Company, New York Liu, Q. and Sommer, S. S. (2004). PAP: detection of ultra rare mutations depends on P* oligonucleotides: "sleeping beauties" awakened by the kiss of pyrophosphorolysis. *Hum Mutation* 23(5):426-436.

Newton, C. R. et al. (1989). Analysis of any point mutation in DNA. The amplification refractory mutation system (ARMS). *Nucl Acids Res* 17(7):2503-2516.

Nichols, W. C. et al. (1989). Direct sequencing of the gene for Maryland/German familial amyloidotic polyneuropathy type II and genotyping by allele-specific enzymatic amplification. *Genomics* 5(3):535-540.

Parsons, B. L. and Heflich, R. H. (1997). Genotypic selection methods for the direct analysis of point mutations. *Mutation Res* 387(2):97-121.

Shi, J. et al. (2007). Detection of ultrarare somatic mutation in the human TP53 gene by bidirectional pyrophosphorolysis-activated polymerization allele-specific amplification. *Hum Mutation* 28(2):131-136.

Sommer, S. S. et al. (1989). A novel method for detecting point mutations or polymorphisms and its application to population screening for carriers of phenylketonuria. *Mayo Clinic Proceedings* 64(11): 1361-1372.

Wu, D. Y. et al. (1989). Allele-specific enzymatic amplification of beta-globin genomic DNA for diagnosis of sickle cell anemia. *Proc Natl Acad Sci USA* 86(8):2757-2760.

What is claimed is:

1. A method of detecting presence of and/or amount of one or more donor-positive, recipient-negative polymorphisms in a transplant recipient at different points in time which comprises:
   (a) screening a panel of DNA polymorphisms using bi-directional pyrophosphorolysis activated polymerization (Bi-PAP) to identify one or more donor-positive, recipient-negative DNA polymorphisms;
   (b) obtaining a sample of a transplant recipient at a first point in time;
   (c) isolating DNA from the sample of (b);
   (d) detecting the presence of and/or amount of one or more donor-positive, recipient-negative DNA polymorphisms in the recipient sample of (b) by amplifying the DNA of (c) using Bi-PAP and detecting the presence of and/or the amount of one or more donor-positive, recipient negative DNA polymorphisms in the amplified DNA;
   (e) obtaining a sample of a transplant recipient at a second point in time;
   (f) isolating DNA from the sample of (e); and
   (g) detecting the presence and/or amount of one or more donor-positive, recipient-negative DNA polymorphisms in the recipient sample of (e) by amplifying the DNA of (f) using bi-PAP and detecting the presence of and/or the amount of one or more donor-positive, recipient negative DNA polymorphisms in the amplified DNA;
   wherein the panel of DNA polymorphisms comprises Rs396, Rs7289, Rs7825, Rs11793, Rs11901, Rs33296, Rs153887, Rs4261, Rs30209, Rs31224, and Rs156988.

2. The method of claim 1, wherein steps (e)-(g) are repeated one or more times to detect the presence of and/or amount of one or more donor-positive, recipient-negative cells in a transplant recipient at a third and greater point in time.

3. The method of claim 2, wherein the transplant recipient has received transplanted islet cells.

4. The method of claim 1, wherein the transplant recipient has received transplanted islet cells.

5. The method of claim 1, wherein the one or more donor-positive, recipient-negative DNA polymorphism identified is Rs396, and the bi-directional pyrophosphorolysis activated polymerization is performed at the first and second time points using four primers, wherein the primers have the sequences comprising SEQ ID NO: 2-5.

6. The method of claim 1, wherein the one or more donor-positive, recipient-negative DNA polymorphism identified is Rs7289, and the bi-directional pyrophosphorolysis activated polymerization is performed at the first and second time points using four primers, wherein the primers have the sequences comprising SEQ ID NO: 7-10.

7. The method of claim 1, wherein the one or more donor-positive, recipient-negative DNA polymorphism identified is Rs7825, and the bi-directional pyrophosphorolysis activated polymerization is performed at the first and second time points using four primers, wherein the primers have the sequences comprising SEQ ID NO: 12-15.

8. The method of claim 1, wherein the one or more donor-positive, recipient-negative DNA polymorphism identified is Rs11793, and the bi-directional pyrophosphorolysis activated polymerization is performed at the first and second time points using four primers, wherein the primers have the sequences comprising SEQ ID NO: 17-20.

9. The method of claim 1, wherein the one or more donor-positive, recipient-negative DNA polymorphism identified is Rs11901, and the bi-directional pyrophosphorolysis activated polymerization is performed at the first and second time points using four primers, wherein the primers have the sequences comprising SEQ ID NO: 22-25.

10. The method of claim 1, wherein the one or more donor-positive, recipient-negative DNA polymorphism identified is Rs33296, and the bi-directional pyrophosphorolysis activated polymerization is performed at the first and second time points using four primers, wherein the primers have the sequences comprising SEQ ID NO: 27-30.

11. The method of claim 1, wherein the one or more donor-positive, recipient-negative DNA polymorphism identified is Rs153887, and the bi-directional pyrophosphorolysis activated polymerization is performed at the first and second time points using four primers, wherein the primers have the sequences comprising SEQ ID NO: 32-35.

12. The method of claim 1, wherein the one or more donor-positive, recipient-negative DNA polymorphism identified is Rs4261, and the bi-directional pyrophosphorolysis activated polymerization is performed at the first and second time points using four primers, wherein the primers have the sequences comprising SEQ ID NO: 37-40.

13. The method of claim 1, wherein the one or more donor-positive, recipient-negative DNA polymorphism identified is Rs30209, and the bi-directional pyrophosphorolysis activated polymerization is performed at the first and second time points using four primers, wherein the primers have the sequences comprising SEQ ID NO: 42-45.

14. The method of claim 1, wherein the one or more donor-positive, recipient-negative DNA polymorphism identified is Rs31224, and the bi-directional pyrophosphorolysis activated polymerization is performed at the first and second time points using four primers, wherein the primers have the sequences comprising SEQ ID NO: 47-50.

15. The method of claim 1, wherein the one or more donor-positive, recipient-negative DNA polymorphism identified is Rs156988, and the bi-directional pyrophosphorolysis activated polymerization is performed at the first and second time points using four primers, wherein the primers have the sequences comprising SEQ ID NO: 52-55.

* * * * *